US009131079B2

(12) United States Patent
Oklejas

(10) Patent No.: US 9,131,079 B2
(45) Date of Patent: Sep. 8, 2015

(54) SYSTEM AND METHOD FOR PROVIDING A TELEVISION NETWORK CUSTOMIZED FOR AN END USER

(71) Applicant: Robert A. Oklejas, Monroe, MI (US)

(72) Inventor: Robert A. Oklejas, Monroe, MI (US)

( * ) Notice: Subject to any disclaimer, the term of this patent is extended or adjusted under 35 U.S.C. 154(b) by 0 days.

(21) Appl. No.: 14/604,424

(22) Filed: Jan. 23, 2015

(65) Prior Publication Data
US 2015/0143449 A1 May 21, 2015

Related U.S. Application Data

(63) Continuation-in-part of application No. 13/416,390, filed on Mar. 9, 2012, now Pat. No. 8,978,087, which is a continuation of application No. 12/564,785, filed on Sep. 22, 2009, now Pat. No. 8,151,315, which is a continuation-in-part of application No. 11/275,960, filed on Feb. 7, 2006, now abandoned, application No. 14/604,424, which is a continuation-in-part of application No. 13/677,100, filed on Nov. 14, 2012.

(60) Provisional application No. 60/650,674, filed on Feb. 7, 2005, provisional application No. 61/559,436, filed on Nov. 14, 2011, provisional application No. 61/543,702, filed on Oct. 5, 2011, provisional application No. 61/931,323, filed on Jan. 24, 2014.

(51) Int. Cl.
H04N 7/10 (2006.01)
H04N 7/025 (2006.01)
H04N 7/00 (2011.01)
A61M 21/02 (2006.01)
H04N 7/173 (2011.01)
H04N 21/2187 (2011.01)
H04N 21/234 (2011.01)
(Continued)

(52) U.S. Cl.
CPC .............. H04N 7/002 (2013.01); A61M 21/02 (2013.01); G06Q 30/00 (2013.01); H04N 5/247 (2013.01); H04N 7/17318 (2013.01); H04N 7/181 (2013.01); H04N 21/2187 (2013.01); H04N 21/23424 (2013.01); H04N 21/44016 (2013.01); H04N 21/47202 (2013.01); H04N 21/6587 (2013.01); H04N 21/812 (2013.01); A61M 2021/005 (2013.01); A61M 2021/0027 (2013.01)

(58) Field of Classification Search
CPC .......................... H04N 21/812; H04N 21/4532
USPC ...................................... 725/34–36
See application file for complete search history.

(56) References Cited

U.S. PATENT DOCUMENTS 4,264,925 A 4/1981 Freeman et al.
4,724,491 A 2/1988 Lambert
(Continued)

FOREIGN PATENT DOCUMENTS

EP 1415470 B1 11/2006

OTHER PUBLICATIONS http://www.moviesunlimited.com/musite/product.asp?sku=D18836 2004.

(Continued)

Primary Examiner — Hunter B Lonsberry
(74) Attorney, Agent, or Firm — Howard & Howard Attorneys PLLC

(57) ABSTRACT

A hybrid audio and video system and method of providing a television network customized for an end user at an end user location are provided. A video signal feed includes visual content. An audio signal feed includes audio content. A third signal feed includes promotional content about the end user. Specific visual content, audio content, and promotional content are electronically selected. The visual content, audio content, and promotional content are electronically combined in response to the selections to create an output feed. The selected visual content, audio content, and promotional content of the output feed through the television network at the end user location.

20 Claims, 3 Drawing Sheets

(51) Int. Cl.
*H04N 21/44* (2011.01)
*H04N 21/472* (2011.01)
*H04N 21/81* (2011.01)
*H04N 5/247* (2006.01)
*H04N 7/18* (2006.01)
*H04N 21/6587* (2011.01)
*G06Q 30/00* (2012.01)
*A61M 21/00* (2006.01)

(56) References Cited

U.S. PATENT DOCUMENTS

| | | | |
|---|---|---|---|
| 5,571,057 | A | 11/1996 | Ayers |
| 5,761,601 | A | 6/1998 | Nemirofsky et al. |
| 5,979,757 | A | 11/1999 | Tracy et al. |
| 6,029,045 | A | 2/2000 | Picco et al. |
| 6,075,551 | A | 6/2000 | Berezowski et al. |
| 6,256,401 | B1 | 7/2001 | Whited |
| 6,324,694 | B1 | 11/2001 | Watts et al. |
| 6,414,716 | B1 | 7/2002 | Kawai |
| 6,418,234 | B1 | 7/2002 | Whited |
| 6,489,986 | B1 | 12/2002 | Allen |
| 6,493,876 | B1 | 12/2002 | DeFreese et al. |
| 6,526,575 | B1 | 2/2003 | McCoy et al. |
| 6,529,233 | B1 | 3/2003 | Allen |
| 6,684,399 | B1 | 1/2004 | Grooters |
| 6,732,028 | B2 | 5/2004 | Vanstory et al. |
| 6,799,326 | B2 | 9/2004 | Boylan, III et al. |
| 7,444,659 | B2 | 10/2008 | Lemmons |
| 7,587,747 | B2 | 9/2009 | Maguire, Jr. |
| 7,826,444 | B2 | 11/2010 | Irvin |
| 7,889,724 | B2 | 2/2011 | Irvin |
| 7,934,230 | B2 | 4/2011 | Badt, Jr. et al. |
| 8,151,315 | B2 | 4/2012 | Oklejas |
| 2001/0013680 | A1 | 8/2001 | Chaaban |
| 2002/0028002 | A1 | 3/2002 | Whited |
| 2002/0051958 | A1 | 5/2002 | Khalsa |
| 2002/0087976 | A1 | 7/2002 | Kaplan et al. |
| 2002/0144279 | A1 | 10/2002 | Zhou |
| 2002/0171770 | A1 | 11/2002 | Wendt et al. |
| 2003/0225095 | A1 | 12/2003 | McCulloch et al. |
| 2003/0226150 | A1 | 12/2003 | Berberet et al. |
| 2004/0032434 | A1 | 2/2004 | Pinsky et al. |
| 2004/0044724 | A1 | 3/2004 | Bell et al. |
| 2004/0044725 | A1 | 3/2004 | Bell et al. |
| 2004/0230486 | A1 | 11/2004 | Greenlee |
| 2005/0060759 | A1 | 3/2005 | Rowe et al. |
| 2005/0078172 | A1 | 4/2005 | Harville et al. |
| 2005/0169314 | A1 | 8/2005 | Beaudoin et al. |
| 2005/0204387 | A1 | 9/2005 | Knudson et al. |
| 2005/0251565 | A1 | 11/2005 | Weel |
| 2005/0262542 | A1 | 11/2005 | DeWeese et al. |
| 2006/0176374 | A1 | 8/2006 | Oklejas |
| 2007/0174873 | A1 | 7/2007 | Griggs |
| 2009/0044217 | A1 | 2/2009 | Lutterbach et al. |
| 2010/0088730 | A1 | 4/2010 | Oklejas |

OTHER PUBLICATIONS http://www.amazon.com/Oreade-Music-Waterfalls-DVD-Various-Artists/db/B0000C318A, released in 2003, see various coments dated in 2004.

http://www.imdb.com/title/tt0784945/ 2004.

Article entitled "List of SportsCenter segments and secials" from Wikipedia, the free encyclopedia at http://web.archive.org/web/20071215022309/http://en.wikipedia.org/wiki/List_of_SportsCenter_segments_and_specials#P On Oct. 21, 2010; 7 pages.

Search Report for International Application No. PCT/US2010/048238; mailed Nov. 3, 2010; 2 pages.

Written Opinion for International Application No. PCT/US2010/048238; mailed Nov. 3, 2010; 6 pages.

Second Written Opinion for International Application No. PCT/US2010/048238; mailed Nov. 7, 2011; 22 pages.

Park et al., Brand Attachment and Brand Attitude Strength: Conceptual and Empirical Differentiation of Two Critical Brand Equity Drivers; Journal of Marketing, vol. 74, Nov. 2010, pp. 1-17.

Pham et al., Relaxation Increases Monetary Valuations; Journal of Marketing Research, vol. XLVIII, Oct. 2011, pp. 814-826.

Innerscope Research and Fox Broadcasting Company Debut Biometric Study Scientifically Validating the Creation of Brand Equity through Immersive Media Exposure; News Corporation, May 2011, pp. 1-3.

SYSTEM AND METHOD FOR PROVIDING A TELEVISION NETWORK CUSTOMIZED FOR AN END USER

CROSS-REFERENCE TO RELATED APPLICATIONS

The present application is a continuation-in-part of U.S. application Ser. No. 13/416,390, filed Mar. 9, 2012, which is a continuation of U.S. application Ser. No. 12/564,785, filed Sep. 22, 2009, which is now U.S. Pat. No. 8,151,315, which is a continuation-in-part of U.S. application Ser. No. 11/275, 960 filed Feb. 7, 2006, which claims priority to U.S. Provisional Application Ser. No. 60/650,674, filed Feb. 7, 2005, each of which are hereby incorporated by reference. The present application is further a continuation-in-part of U.S. application Ser. No. 13/677,100, filed Nov. 14, 2012, which claims priority to U.S. Provisional Application Ser. No. 61/559,436, filed Nov. 14, 2011, and U.S. Provisional Application Ser. No. 61/543,702, filed Oct. 5, 2011, each of which are hereby incorporated by reference. The present application further retains priority to U.S. Provisional Application Ser. No. 61/931,323 filed Jan. 24, 2014, which is hereby incorporated by reference.

FIELD OF THE INVENTION

The present invention relates to a hybrid audio/visual television network that is uniquely customized for an end user.

BACKGROUND

Typically, programming offered by a traditional television network company is directed to various programming interspaced with advertisements purchased by companies and intended to reach broad geographical markets. These systems have very limited ability to customize programming and advertising specific to an end user entity, such as a hospital, restaurant, a doctor's office, an auto dealer, and the like. It has been neither practical, readily available, nor cost effective to provide specific programming and information embedded in the network programming directed to a specific end user.

Video sharing services on the Internet, such as YOU-TUBE®, and the like nonetheless suffer from these same deficiencies. Such videos are presented to the Internet market as a whole and the video/audio content in such videos is not customized for the end viewer.

Hybrid audio and video systems provide an alternative to typical television programming and video sharing service programming. Such systems offer a mix of audio broadcasting with video content. However, there is currently no effective low cost solution for offering customized end user branded programming with directed advertising and information specific to the end user entity.

Moreover, there are dozens of end user entities that are involved in or produce stress for their visitors, e.g., doctors, dentists, banks, attorneys, police stations, fire stations, military bases, prisons, correctional facilities, and the like. Yet, research has shown that people in relaxed states have a 15-20% higher perceived monetary value of a product or service and exhibit better long-term visual memorization. There are no hybrid audio and video systems in the prior art that exploit this research.

US Patent Application Publication No. US 2009/0044217 discloses the insertion of replacement commercials in an otherwise unmodified television program. In other words, the system allows insertion of customized commercial spots in lieu of the original spots. However, the system of US 2009/0044217 is not a hybrid audio and video system and is confined to the realm of traditional television broadcasting. The system of US 2009/0044217 utilizes satellites, uplink and down link satellite antennas, ground based head ends, cue tones and digital program insert nodes. These systems are conventionally very high cost, both in initial capital and operating cost. Moreover, the system of US 2009/0044217 fails to provide customization of long form content to produce a branded network specific to the end user entity. Additionally, the system of US 2009/0044217 is not configured to provide continuous content that is designed to cause viewers to be in a relaxed state of mind.

SUMMARY AND ADVANTAGES

A hybrid audio and video system for providing a television network customized for an end user at an end user location is provided. A video signal feed includes visual content. An audio signal feed includes audio content. A third signal feed includes promotional content about the end user. A control node is configured to access the feeds and receive electronic selections of specific visual content, audio content, and promotional content. The control node electronically combines the selected visual content, audio content, and promotional content in response to the selections to generate an output feed for presenting the selected visual content, audio content, and promotional content through the television network with an audiovisual display at the end user location.

A method of providing a television network customized for an end user at an end user location is also provided. A video signal feed including visual content is provided. An audio signal feed including audio content is provided. A third signal feed including promotional content about the end user is provided. Specific visual content, audio content, and promotional content are electronically selected. The visual content, audio content, and promotional content are electronically combined in response to the selections to create an output feed. The selected visual content, audio content, and promotional content of the output feed are presented through the television network at the end user location.

The system and method provide a customizable branded network for the end user. By providing the third signal feed with promotional content about the end user, the system and method further advance hybrid audio and video systems. More specifically, the system and method allow customization of direct programming to include end user content specific to the entity using the system. The system and method provide a low cost solution for integrating custom content into programming and a low cost alternative to costly programming packages and systems currently available. The end user has complete control to customize the audio, video, and promotional content. Through these features, the system and method increase branding for the end user and increase perception by viewers at the end user location. The private custom branded television network offers an affordable, effective and flexible television-based communication network that can be uniquely tailored to the needs and desires of the end user, regardless of the size of the end user entity.

Other objects and features of the present invention will become apparent when viewed in light of the detailed description of the preferred embodiments when taken in conjunction with the attached drawings and appended claims.

BRIEF DESCRIPTION OF THE DRAWINGS

The present invention will become more fully understood from the detailed description and the accompanying drawings, wherein.

DETAILED DESCRIPTION

Figure 1:
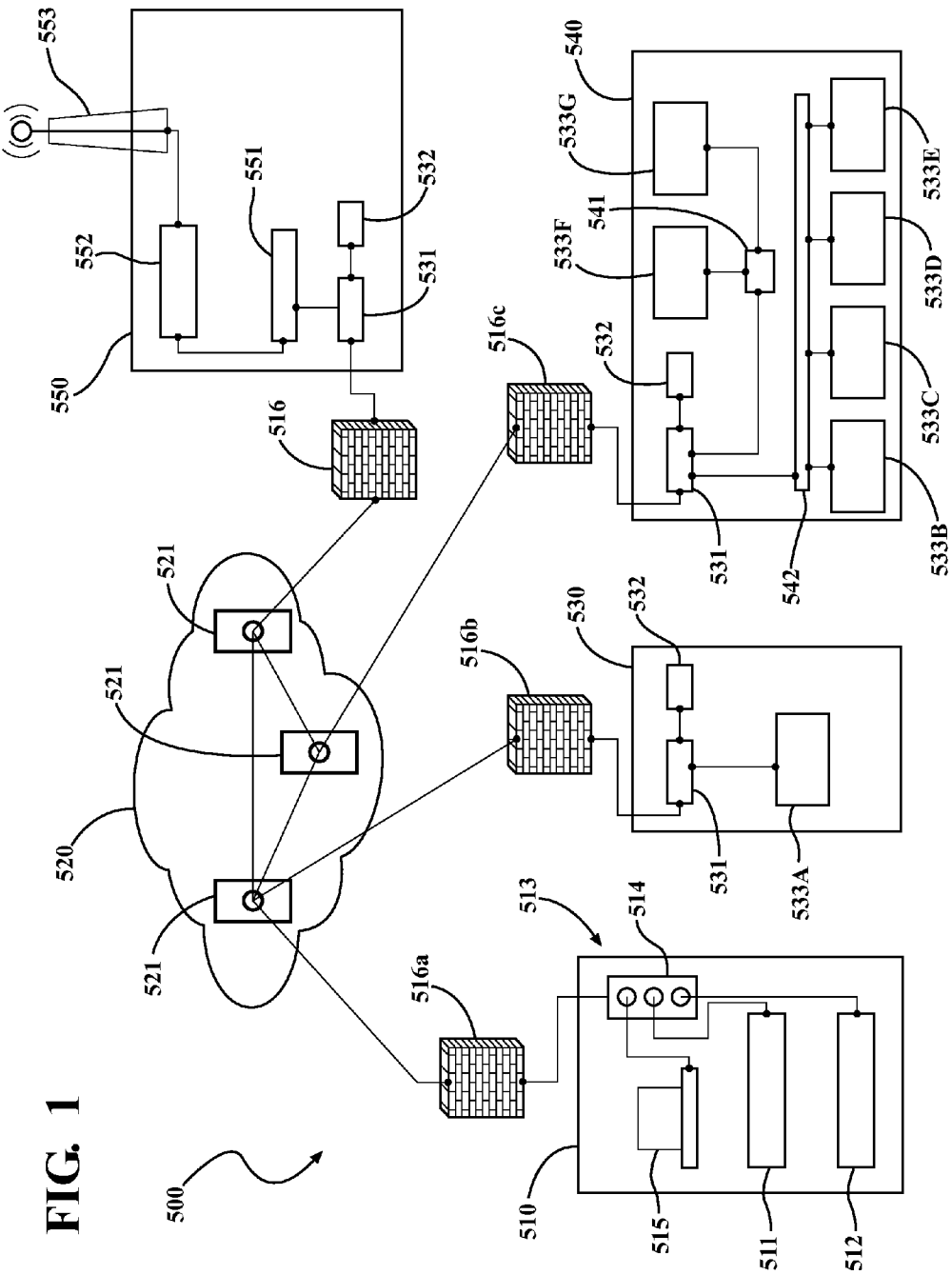
FIG. 1 is a system diagram of the hybrid audio and video system according to one embodiment.

In the following figures, wherein like reference numerals are used to identify identical components in the various views and embodiments, a hybrid audio and video system is illustrated at 500 in FIG. 1 and a method of utilizing the system 500 is described throughout. The hybrid audio and video system 500 and method are for customizing audiovisual content at an end user location. The hybrid audio and video system 500 and method providing a television network customized for an end user at an end user location.

The end user is any entity, business, corporation, organization, community, good/service provider, individual enterprise, television network, governmental agency, place of worship, and the like. The end user location 530 is affiliated with the end user according to any suitable manner. For example, the end user location 530 may be owned, operated, or occupied by the end user, and the like. Examples of the end user location 530 include, but are not limited to, a hospital, a restaurant, an office, a dealership, a library, a hotel, a spa or health club, a transportation location or vehicle, and the like. The system 500 and method may be utilized with any suitable size end user entity. Such entities may have any tens, hundreds, or thousands of employees, patrons, and/or viewers. The end user location may be stationary or mobile. Those skilled in the art appreciate that the end users and associated locations listed herein are provided as examples and that the scope of the invention includes end users and locations other than those listed herein.

Figure 3:
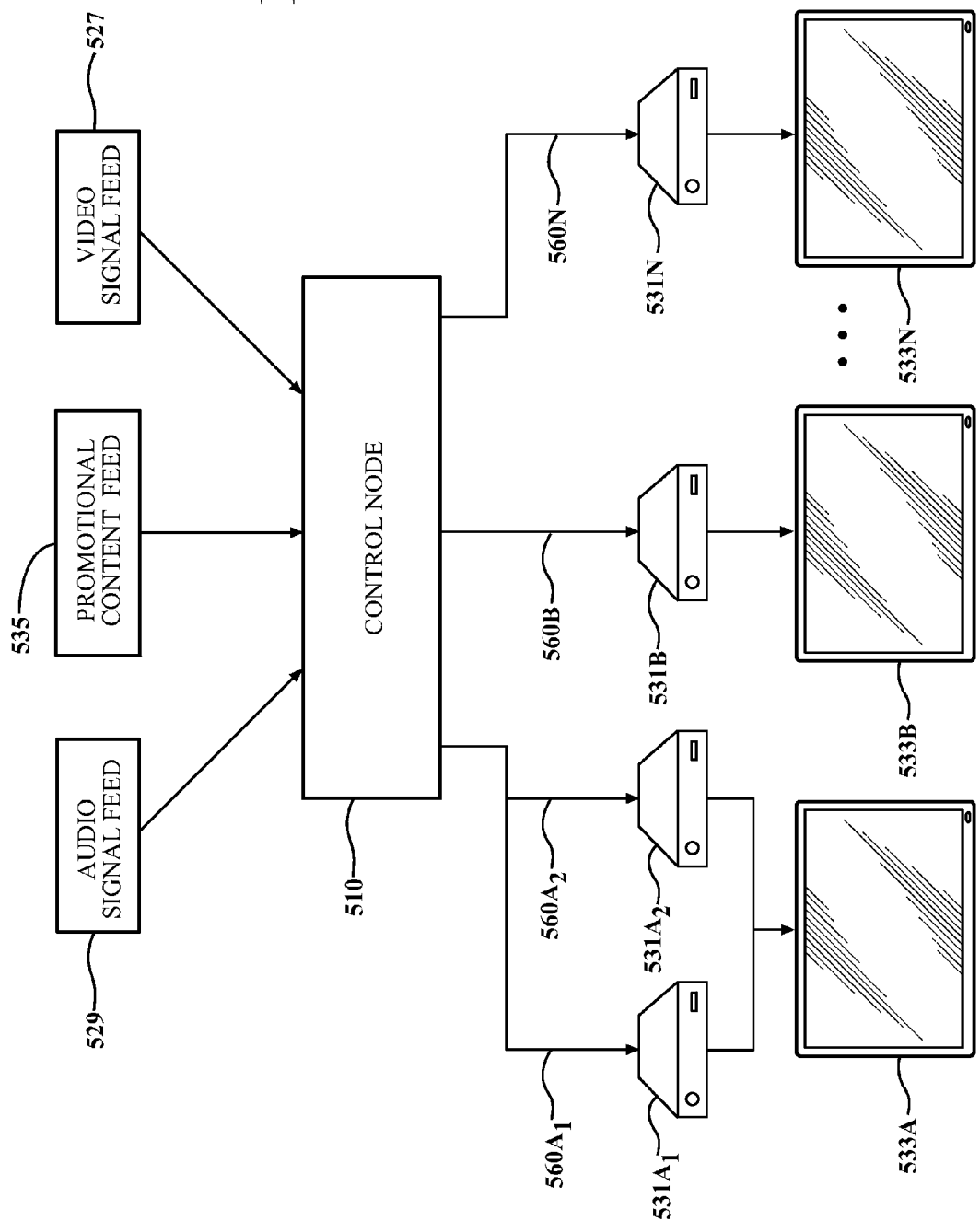
FIG. 3 is a system diagram of the hybrid audio and video and feeds controlled and customized by the same, according to one embodiment.

As shown in FIGS. 1 and 3, the system 500 includes a control node 510. A control device 531, in communication with the control node 510, is located the end user location 530. Communication between the control device 531 and the control node 510 may be Internet based and accessed through the Internet, as described below. In some embodiments, the control node 510 is cloud based. The control node 510 may be located at the central location 513, as shown in FIG. 1. Alternatively, the control node 510 may be located at end user location 530. In yet another embodiment, the control node 510 may be located partially at the central location 513 and partially at the end user location 530. Furthermore, the control node 510 may be controlled via the Internet, central location 513, end user location 530, and any combination thereof.

At the end user location 530, the control device 531 is in communication with an audiovisual display 533. In one example, the audiovisual display 533 is a television monitor that includes, or is attached to, an audio system. In another embodiment, the audiovisual display 533 is a computer system. In yet another embodiment, the audiovisual display 533 is a portable electronic device, such as a smart phone, tablet, laptop, and the like. Those skilled in the art appreciate that audiovisual display 533 may have other configurations not described herein without departing from the scope of the invention.

The system 500 is designed to provide a customizable media platform that is a branded network (hereinafter "Private Television Network" or "PTN") for the end user entity. Generally, viewers, consumers, patrons, or employees at the end user location 530 experience the PTN through the audiovisual display 533 at the end user location 530.

The control node 510 includes digital media storage and software configured for production and play out functions. In FIG. 1, the control node 510 includes a master control workstation 515 or central media studio. The master control workstation 515 controls the PTN. For example, the master workstation 515 may create the playlist for the PTN and customize content for the PTN, as described below. A central media platform originator may create and the deliver customized media through the control node 510. The control node 510 includes a production archive main server 511 and a production archive back-up server 512. The servers 511, 512 and the master control workstation 515 are each connected to a router 514. The router 514 is connected to the Internet, and more specifically, an Internet-based cloud 520. A firewall 516a is provided between the Internet 520 and router 514 for protecting the control node 510. The PTN is Internet connected and controlled.

Content delivery network ("CDN") servers 521 transfer hybrid audiovisual content data through the cloud 520. The CDN servers 521 connect to control devices 531 at end user locations 530, 540. In one embodiment, locations 530, 540 relate to the same end user. In another embodiment, locations 530, 540 relate to different end users. In FIG. 1, for example, location 530 is a smaller facility and location 540 is a larger facility. Firewalls 516b, 516c are provided respectively between the CDN servers 521 and the control devices 531 at each end user locations 530, 540.

The PTN incorporates the master control workstation 515 for producing hybrid digital audio and video content. The hybrid audiovisual content is long form content that is preferably in the form of non-stop broadcasting of media content. The system 500 distributes the hybrid audiovisual content to the end user location 530. The PTN incorporates the central media studio that produces digital audio and video content. One embodiment of such a platform is the eScapes network which provides non-stop hybrid audiovisual content based on the hybrid television audio system/therapeutic benefit television system described in U.S. patent application Ser. No. 11/275,960, which is now U.S. Pat. No. 8,151,315, the disclosure of which is incorporated herein by reference in its entirety to the extent it does not conflict with the general scope of the present invention.

As shown in FIG. 3, the hybrid audiovisual content includes content from three separate feeds or electronic sources 527, 529, 535. Thus, hybrid audiovisual content is unlike traditional television broadcasting programming which provides content that is pre-produced with audio and visual elements, and hence, not customizable. The control node 510 is configured to access these feeds 527, 529, 535.

Figure 2:
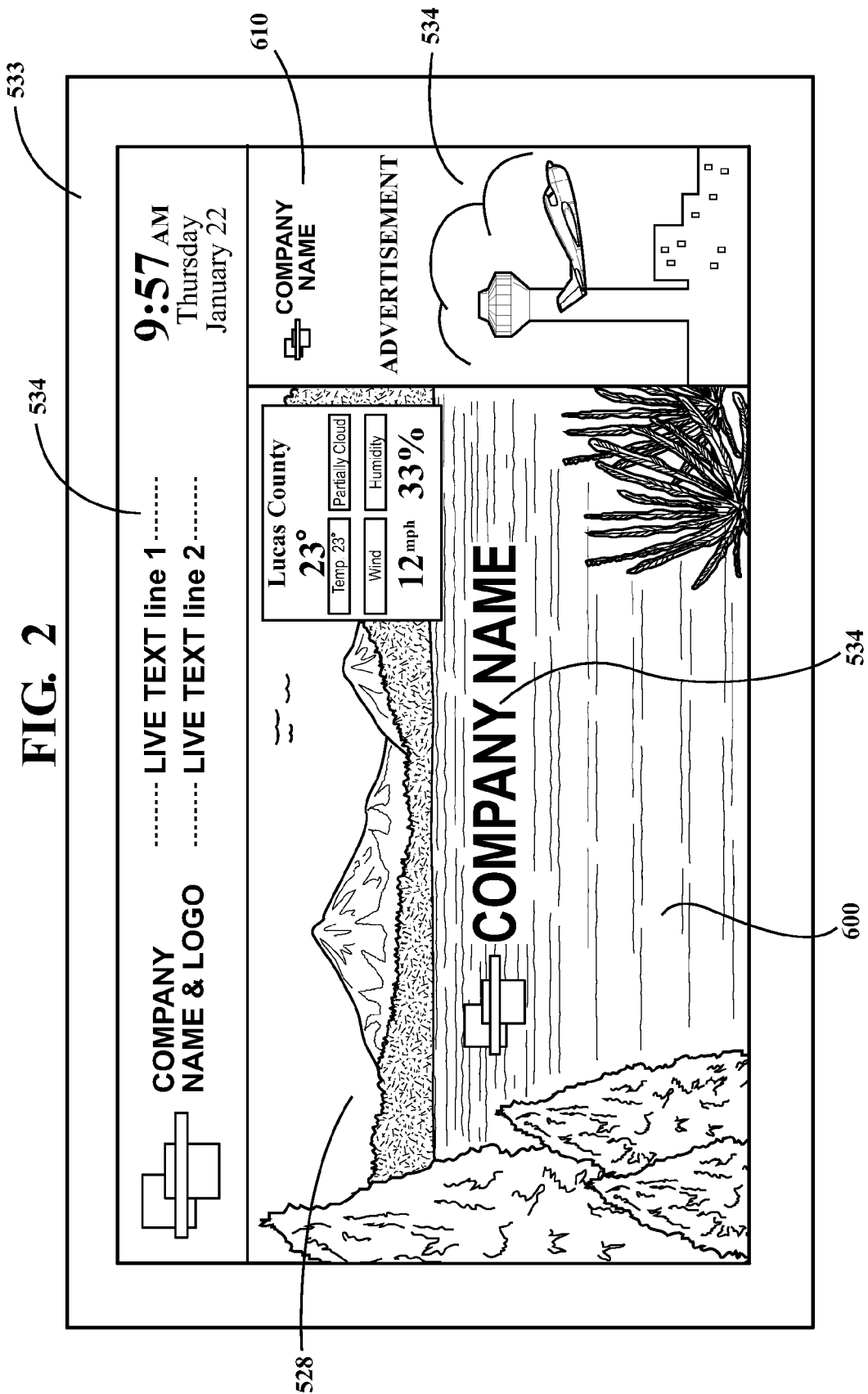
FIG. 2 is a sample screenshot of an audiovisual display presenting audiovisual content customized by the hybrid audio and video system and method according to one example.

As shown in FIG. 3, the hybrid audiovisual content comprises content from a video signal feed 527, which is a first electronic feed. The video signal feed 527 conveys visual content 528, as shown in FIG. 2. More specifically, the visual content 528 is therapeutic and designed to provide a relaxing experience for persons presented with the visual content 528 at the end user location 530. The visual content is digital, electronic based content. In one example, as shown in FIG. 2, the visual content 528 is a natural landscape. The visual content 528 may be still images or video. In one embodiment, the video feed 527 is an electronically accessible library comprising various visual content 528 content. Such visual content 528 provides aesthetically appealing qualities with an additional emphasis on scenes that produce a relaxation or calming effect on the human psyche. Examples of such visual content 528 may include, but are not limited to, environmental scenes, natural wonders, artistic scenes, holiday scenes, marine scenes, city skylines, wildlife content, majestic landscape or seascapes, and the like. The visual content 528 may be live or prerecorded. The visual content 528 may be viewed in real time, or at the time of day or night when it was prerecorded. The visual content 528 may be modified based on different levels of customization. In one embodiment, the visual content 528 is generic to all subscribers. In another embodiment, the visual content 528 includes content that is specific to the end user. For example, the visual content 528 may include content relating to property affiliated with the end user, and the like. The visual content 528 may be derived from any suitable source for providing visual content, such as studios, computer databases, and Internet sources. Those skilled in the art appreciate that the visual content 528 may have other configurations not described herein without departing from the scope of the invention.

The hybrid audiovisual content comprises content from an audio signal feed 529, which is a second electronic feed, as shown in FIG. 3. The audio signal feed 529 conveys audio content, and more specifically, audio content to complement the visual content 528. The audio content is digital, electronic based audio content. The audio content is therapeutic audio for providing a relaxing experience for persons presented with the audio at the end user location 530. In one embodiment, the audio feed 529 is an electronically accessible library of audio content. Such audio content can be selected to promote relaxation/therapeutic effects. Examples of such audio content include, but are not limited to surf, running water, rain, bird songs, appropriate music genres, and the like. Such music genres may be slow tempo, mostly instrumental music genres that are intended to produce a relaxation state in the viewer/listener. Other sounds such as lighthouse foghorns, ship whistles, weather sounds of wind, thunder can add to the realism and authenticity of the video presentation. In many instances, the visual content 528 is of a subject and the audio content is environmental sound relating to the subject. For example, if the visual content 528 is of an ocean, the corresponding audio content is the environmental sound of the ocean. The audio content may be modified based on different levels of customization. In one embodiment, the audio content is a generic to all end users. In another embodiment, the audio content contains content that is specific to the end user. For example, the audio content may contain announcements, advertisements, or comments about the end user. The audio content may be live or prerecorded. The audio content may be derived from any suitable source for providing audio content, such as studios, computer databases, and Internet sources. Those skilled in the art appreciate that the audio content may have other configurations not described herein without departing from the scope of the invention.

The hybrid audiovisual content further comprises promotional content 534 from a third signal feed 535, which is a third electronic feed, as shown in FIG. 3. The third signal feed 535 conveys promotional content 534 about the end user. The promotional content is digital, electronic based content. Examples of the promotional content 534 are shown in FIG. 2. Promotional content about the end user includes at least one of visual and audiovisual content. In other words, the promotional content about the end user may be purely visual content or audiovisual content. The third signal feed 535 may be an electronically accessible library comprising promotional content templates that can be customized. In one embodiment, promotional content 534 includes commercial advertisement and/or branding content relating to the end user. The promotional content 534 may take various configurations, including but not limited to branding information, commercials, a company trademark, external or internal advertisements, continuous RSS ("Real Simple Syndication") or XML feed text, social media information, text messages, crawling information ribbons, static images or dynamic video, business hours of operation, announcements, and the like. As shown in FIG. 2, the promotional content 534 may include live text strings. The strings may be placed on various different lines, e.g., lines 1 and lines 2.

In an example wherein the end user is a hospital, the promotional content 534 may be general hospital messages, public service announcement, self-help messages, spiritual/comforting message, and the like. In this same example, promotional content 534 may alternatively be commercial advertisements for external related companies, such as medical service companies, pharmaceutical companies, insurance companies, etc. Those skilled in the art appreciate that the list of promotional content 534 described herein are examples and that the invention may utilize other promotional content 534 not described herein. The promotional content 534 may be live or prerecorded. The promotional content 534 may be derived from any suitable source for providing promotional content, such as studios, computer databases, and Internet sources. Those skilled in the art appreciate that the promotional content may have other configurations not described herein without departing from the scope of the invention.

The promotional content 534 may be modified based on different levels of customization. The promotional content 534 is specific to the end user. However, certain add-ons or additional promotional features may be available depending on end user subscriptions. For example, one level of customization for the promotional content 534 may allow only text feeds while a higher level of customization may allow promotional graphics, and the like.

The feeds 527, 529, 535 are separate and distinct feeds which originate from separate sources. The control node 510 is configured to access the feeds 527, 529, 535 on demand. By doing so, the control node 510 is able to selectively choose content from any given feed 527, 529, 535.

The control node 510 is further configured to receive electronic selections of specific visual content 528, audio content, and promotional content 534. In one embodiment, the control node 510 is connected to the Internet 520 and the electronic selections are received through the Internet 520. The electronic selections may be made by the end user. For example, the end user may log on through an Internet-based account to make selections. The end user may take partial or full control of the control device 531 at the end user location 530. To do so, the end user utilizes any suitable device connected to the Internet 520. For instance if the end user desires to display a greeting to a customer/viewer at its facility 530 the end user may log on with a user name and password to manage control device 531 and customize and select content from the feeds 527, 529, 535, and other features. In another embodiment, electronic selections occur automatically according to predetermined rules, programs, and the like.

The control node 510 combines, mixes, and customizes the feeds 527, 529, 535 to produce customized content for the PTN at the end user location 530. The control node 510 is configured to control the video signal feed 527, audio signal feed 529, and third signal feed 535. For example, the control node 510 may edit, mix, combine, or modify the feeds 527, 529, 535 in any suitable manner to produce the hybrid audiovisual content. The control node 510 electronically combines the selected visual content 528, audio content, and promotional content 534 in response to the selections. The control node 510 may combine, mix, or customizes the feeds 527, 529, 535 according to any suitable configuration and in any suitable order.

After doing so, the control node 510 generates an output feed 560. The control node 510 is configured to communicate the output feed 560, or any variation thereof, to the control device 531 at the end user location 530. The control device 531 receives the output feed 560. The audiovisual display 533 located at the end user location 530 electronically presents the selected visual content 528, audio content, and promotional content 534, thereby providing the customized PTN.

The control node 510 may produce a plurality of output feeds 560A-560N, as shown in FIG. 3. When multiple displays 533A-533N are utilized, as shown in FIG. 3, each display 533A-533N may provide content from separate output feeds 560A-560N.

In some instances, the third signal feed 535 may be integrated or combined wholly or partially with audio feed 529 and or the video feed 527. Additionally, the visual content 528 and the promotional content 534 may be combined during playback. For example, as shown in FIG. 2, the promotional content 534 of the company name is played atop the visual content 528 to create a branding effect for the company. To supplement this configuration, the company name is further provided continuously in a branding bar located above the visual content 528. The branding bar reiterates to viewers that the PTN is specifically customized for the company.

Informative content may be combined with the visual content 528 or promotional content 534 to supplement the PTN programming. Such informative content can be integrated as additional feature/enhancement to the PTN. Such information includes, but is not limited to, time, day, date, and weather information, as shown in FIG. 2. For example, the weather information is provided as an external feed and may be any RSS/XML media feed, as described.

Such information may be considered part of, or integrated with the visual content 528. However, such information generally is not promotional content 534 as such information is not promotional in nature.

The hybrid audiovisual content comprises the majority of the PTN's programming schedule. The hybrid audiovisual content allows for the economical creation of thousands of hours of high functioning, high testing programming, thus making very limited distribution platforms affordable.

The control device 531 includes a high definition media player (HDMP). The HDMP is configured to receive, store and locally play out of the audiovisual content from the output feed 560. A media storage device 532 is locally connected to and associated with the control device 531. The media storage device 532 is any suitable media storage device. The media storage device 532 may be internal to or external to the control device 531. The media storage device 532 may also be connected to an external hard drive.

The media storage device 532 stores the hybrid audiovisual content. The media storage device 532 may store at least one, or each, of the visual, audio, or promotional content 534. In one embodiment, the media storage device 532 contains hundreds of hours of hybrid audiovisual content. The content on the storage device 532 may be refreshed at predetermined frequencies. The media storage device 532 may be utilized to supplement the control device 531, which may have an internal storage capability of only a few hours. Digital files that contain the branding content and local advertising (if any) may be stored locally in the control device 531. Through this configuration, the system 500 and method enable hybrid audiovisual content to play continuously for extended periods, such as days, weeks, or even months. Thus, the system 500 and method eliminate repetitive and continuous looping of content, which is an impediment and drawback to long term viewing of such content.

The control node 510 controls the hybrid audiovisual content remotely. For example, the media storage device 532 may be preloaded with an initial playlist of hybrid audiovisual and other suitable content along with the end user's advertisement and branding content. With connectivity through the Internet cloud, additional and new hybrid audiovisual content plus new branding and advertising messages can be downloaded to the control device 531 and media storage device 532 from the control node 510. The Internet connection allows a master control workstation 515 in the control node 510 to control hybrid audiovisual content, update new hybrid audiovisual content and/or create new play lists as often as required. Thus, the PTN can be controlled from any location having Internet access. Of course, in other embodiments, the PTN may be controlled additionally or alternatively from the control node 510 locally at the central location 513 or end user location 530, as described above.

In the case of a large facility 540, as shown in FIG. 1, one control device 531 can output the customized hybrid audiovisual content to multiple audiovisual displays 533B-533G through signal splitters 541 and internal distribution networks 542. The control device 531 can be supplied in a wireless design, thereby making installation of the Internet connection less intrusive. Each display 533B-533G may be located in a separate area or room at the end user facility 530.

As shown in FIG. 1, the PTN may provide hybrid audiovisual content to terrestrial broadcasters 550 and to cable television distribution systems. Using the terrestrial broadcast as an example, the output from the control device 531 is fed to a signal converter 551, which converts the signal. The signal converter 551 outputs another signal to broadcast equipment 552. The broadcast equipment outputs a signal to antenna 553 for transmission. In the case of cable distribution, the control device 531 signal is played out through the cable medium. If the PTN is widely spaced geographically, then other control devices 531 may be employed in each end user location 530.

The control devices 531 can be time synchronized such that each of the displays 533 electronically present the same hybrid audiovisual content at the same time. Alternatively, each control devices 531 can be independently controlled such that displays 533 present different hybrid audiovisual content from one another. The control devices 531 can also be controlled so that different viewers in different time zones or activity schedules see programming appropriate to the time zone they are located in or to the activity that is appropriate to their facility.

Each control device 531 can have hybrid audiovisual customized for the end user. As an example, suppose the end user entity is a health care provider having 8 hospitals, 25 clinics and 400 individual doctor offices at various geographical locations. The control devices 531 at the various locations can have hybrid audiovisual content that is common to all. Additionally or alternatively, each control device 531 can have hybrid audiovisual content that is specific to the respective location. For example, the control devices 531 may contain content common to the entire PTN, but could further have promotional content 534 unique to the hospital. Meanwhile, a doctor's office on the same PTN may have common content, but may further have the doctor's office hours or some content personalized for the particular end user doctor.

In yet another embodiment, control node 510 is configured to control the video signal feed 527, audio signal feed 529 and third signal feed 535, and customize the visual content 528, therapeutic audio content, and promotional content 534 in response to a pre-determined program or predetermined rules.

As shown in FIG. 2, the control device 531, and more specifically, the HDMP is configured to define a first zone 600 for displaying the visual content 528 on the display 533 and a second zone 610 for simultaneously displaying the promotional content 534 on the display 533. The first and second zones 600, 610 may be adjacent to one another and of various customizable shapes and sizes. By doing so, the control device 531 increases the amount of unique information and branding to each location of the PTN. In one embodiment, the first zone 600 is a primary zone occupying the majority of the visual display and the second zone 610 occupies a minority of the visual display. The primary zone 610 displays the therapeutic visual content 528. The secondary zone 610 displays the promotional information. In the second zone 610, timely sale or public service information can be displayed. The zones 600, 610 can change shape or location and content within. The zones 600, 610 can be customized based on the electronic selections. The zones 600, 610 create a relaxing atmosphere where it is very natural for the viewer's eye to leave the first zone 600 and watch a series of graphic messages in the second zone 610. The zones 600, 610 further make branding advertising more effective. The system 500 and method may employ any suitable number of zones.

In some instances, two or more control devices 531 are connected to one display 533, as shown in FIG. 3. For example, as shown in FIG. 3, control devices $531A_1$ and $531A_2$ are connected to display 533A. The viewer may select different inputs (e.g., HDMI 1, HDMI 2, HDMI 3) on the display 533A that are connected to different control devices $531A_1$, $531A_2$. In this manner different output feeds $560A_1$, $560A_2$ can simultaneously be provided to the same display 533A.

The end user can customize time schedules for the various hybrid audiovisual content. The time schedule format can be any suitable time interval that the end user desires. For instance, content episodes could be three minutes, eight minutes, half hour, or one hour. As an example, content may be based on a one-hour program divided into four equal segments. Each segment is 15 minutes long and may contain 13 minutes and 50 seconds of programming content (an individual episode), two 30-second commercials, one 3-second and one 7-second network identification spot. However, it is to be appreciated that other time intervals may be utilized without deviating from the scope of the present invention.

The PTN can be set-up in advance for end users that fall into certain categories. Examples of these categories include, but are not limited to, beauty salons, country clubs, marinas, restaurants, retail automotive part suppliers, businesses, schools, government entities, religious entities, and a multitude of other numerous but widely geographically located organizations. For example, if the category is a country club, the promotional content 534 can be pre-loaded with golfing related products or services. Additional long form content such as golfing instruction videos or golfing news stories can be inserted from time to time.

Additionally, the system 500 and method may be utilized in conjunction with existing platforms utilized by the end user. For example, if an existing corporate platform has limited amounts of business-related content, the system 500 and method can be employed to provide the customized hybrid audiovisual content as filler content when there is no corporate content to be aired. Other television networks could also incorporate custom-branded hybrid audiovisual content under their own name and logo to provide filler content as scheduling requirements demand or as a full time service in a digital broadcast sub channel.

The system 500 and method provide a unique platform as both hybrid audiovisual video and audio components are customized for the specified end user. The system 500 and method provide a conducive but not distracting experiential platform for effective branding and advertising. The system 500 and method create a stress-free environment for patrons of the end user facility by offering therapeutic programming that captures attention of viewers. As such, the system 500 and method enable viewers of the therapeutic audio and video content to be in a more relaxed, less stressful, state of mind. In turn, viewers will exhibit a higher perceived monetary value of a product or service and exhibit better long-term visual memorization. Through this therapeutic and relaxing programming, the system 500 and method enhance message retention. Accordingly, the system and method help to brand the end user and generate revenue.

Additionally, the system 500 and method use the hybrid audiovisual entertainment component to entice the attention of viewers so that when the advertisement or branding message plays after the entertainment content ends, the viewer experiences a television format that is familiar, acceptable and effective. The PTN can be a source of information and entertainment content to the end viewers and a source of advertising revenue and other forms of sales revenue to the entity itself. The system 500 and method do not merely add advertising content to the programming. Instead, the system 500 and method allow creation of custom branding of content to create a television network and programming that carries the brand of the customer within the program content.

Advantages of the invention are apparent from the detailed specification, and thus, it is intended by the appended claims to cover all such features and advantages of the invention, which fall within the true spirit, and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A hybrid audio and video system for providing a television network customized for an end user at an end user location, comprising:
    a video signal feed including visual content;
    an audio signal feed including audio content;
    a third signal feed including promotional content about the end user; and
    a control node configured to access the feeds and receive electronic selections of specific visual content, audio content, and promotional content and electronically combine the selected visual content, audio content, and promotional content in response to the selections to generate an output feed for presenting the selected visual content, audio, and promotional content through the television network with an audiovisual display at the end user location.

2. The hybrid audio and video system of claim 1 wherein the control node is connected to the Internet and the electronic selections are received through the Internet.

3. The hybrid audio and video system of claim 1 wherein the control node is located at a central location that is remote from the end user location.

4. The hybrid audio and video system of claim 1 further including a control device located at the end user location and configured to receive the output feed from the control node.

5. The hybrid audio and video system of claim 4 wherein the control device includes a high definition media player (HDMP) for playing the output feed.

6. The hybrid audio and video system of claim 4 wherein the control device is configured to define a first zone for displaying the visual content on the display and a second zone for simultaneously and separately displaying the promotional content on the display.

7. The hybrid audio and video system of claim 4 wherein a media storage device is locally connected to the control device for storing the visual content, audio content, and promotional content.

8. The hybrid audio and video system of claim 7 wherein the control node is configured to remotely update at least one of the visual content, audio content, and promotional content on the media storage device.

9. The hybrid audio and video system of claim 1 wherein the control node is configured to automatically customize the visual content, audio content, and promotional content according to predetermined rules.

10. The hybrid audio and video system of claim 1 wherein the visual content is of a subject and the audio content is environmental sound relating to the subject.

11. The hybrid audio and video system of claim 1 wherein the promotional content includes at least one of visual and audiovisual content.

12. The hybrid audio and video system of claim 1 wherein the video signal feed includes therapeutic visual content for creating a relaxing experience for persons presented with the visual content at the end user location.

13. The hybrid audio and video system of claim 1 wherein the audio signal feed includes therapeutic audio content for creating a relaxing experience for persons presented with the audio content at the end user location.

14. A method of providing a television network customized for an end user at an end user location, the method comprising:
   providing a video signal feed including visual content;
   providing an audio signal feed including audio content;
   providing a third signal feed including promotional content about the end user;
   electronically selecting specific visual content, audio content, and promotional content;
   electronically combining the visual content, audio content, and promotional content in response to the selections to create an output feed; and
   presenting the selected visual content, audio content, and promotional content of the output feed through the television network at the end user location.

15. The method of claim 14 wherein electronically selecting occurs by the end user.

16. The method of claim 14 wherein electronically selecting occurs automatically according to predetermined rules.

17. The method of claim 14 further including accessing the Internet to make electronic selections.

18. The method of claim 14 wherein presenting includes defining a first zone for displaying the visual content on the display and a second zone for simultaneously and separately displaying the promotional content on the display.

19. A hybrid audio and video system for providing a television network customized for an end user at an end user location, comprising:
   a first electronic source providing visual content for creating a relaxing experience for persons presented with the visual content at the end user location;
   a second electronic source providing audio content for creating a relaxing experience for persons presented with the audio content at the end user location;
   a third electronic source providing promotional content about the end user;
   a control node configured to access the electronic sources and receive electronic selections of specific visual content, audio content, and promotional content and combine the selected visual content, audio content, and promotional content in response to the selections to generate an output feed;
   a control device located at the end user location for receiving the output feed from the control node; and
   an audiovisual display located at the end user location and in communication with the control device for presenting the selected visual content, audio content, and promotional content through the television network.

20. A method of providing a television network customized for an end user at an end user location, the method comprising:
   providing a first electronic source including visual content for creating a relaxing experience for persons presented with the visual content at the end user location;
   providing a second electronic source including audio content for creating a relaxing experience for persons presented with the audio content at the end user location;
   providing a third electronic source including promotional content about the end user;
   electronically selecting specific visual content, audio content, and promotional content;
   electronically combining the visual content, audio content, and promotional content in response to the selections to create an output feed; and
   presenting the selected visual content, audio content, and promotional content of the output feed through the television network at the end user location.

* * * * *